US008478529B2

(12) United States Patent
Al-Ruwais et al.

(10) Patent No.: US 8,478,529 B2
(45) Date of Patent: Jul. 2, 2013

(54) VISIBILITY DETERMINATION IN ENVIRONMENTS CONTAINING AIRBORNE DUST PARTICLES

(75) Inventors: Abdulaziz Salem Al-Ruwais, Riyadh (SA); Abobakr Sultan Ahmed, Riyadh (SA)

(73) Assignee: King Saud University, Riyadh (SA)

( * ) Notice: Subject to any disclaimer, the term of this patent is extended or adjusted under 35 U.S.C. 154(b) by 226 days.

(21) Appl. No.: 12/825,324

(22) Filed: Jun. 28, 2010

(65) Prior Publication Data

US 2011/0320124 A1 Dec. 29, 2011

(51) Int. Cl.
*G01V 3/00* (2006.01)
*G06F 11/00* (2006.01)

(52) U.S. Cl.
USPC ................................ 702/2; 702/189; 702/190

(58) Field of Classification Search
USPC ............................................. 702/2, 189, 190
See application file for complete search history.

(56) References Cited

U.S. PATENT DOCUMENTS

| | | | | |
|---|---|---|---|---|
| 4,613,938 | A * | 9/1986 | Hansen et al. | 702/3 |
| 4,687,337 | A * | 8/1987 | Stewart et al. | 356/437 |
| 5,787,385 | A * | 7/1998 | Tognazzini | 702/3 |
| 6,055,052 | A * | 4/2000 | Lilienfeld | 356/338 |
| 6,330,519 | B1 * | 12/2001 | Sawatari | 702/127 |
| 7,095,337 | B2 * | 8/2006 | Sudou et al. | 340/905 |
| 7,212,252 | B2 * | 5/2007 | Kuznetsov | 348/734 |
| 2003/0197867 | A1 * | 10/2003 | Kwon | 356/437 |
| 2010/0026981 | A1 * | 2/2010 | Spinelli et al. | 356/4.01 |
| 2011/0058167 | A1 * | 3/2011 | Knox et al. | 356/338 |

OTHER PUBLICATIONS

Baumer et al., "Relationship of visibility, aerosol optical thickness and aerosol size distribution in an ageing air mass over South-West Germany", Elsevier, Atmospheric Environment 42 (2008) pp. 989-998.*
"Aerosol Science," Office of the Federal Coordinator for Meterology, 2009; http://oea.larc.nasa.gov/PAIS/Aerosols.html.
Aviation Weather Instruments Dictionary, 2011; http://www.alweatherinc.com/reference/definitions.html.
Bashir et al.; "Prediction of forward scattering of cross-polarization due to dry and moist haboob . . . ," Telecommunication J., 1980; 47(VII):462-467.
Clough et al.; "Atmospheric radiance and transmittance—FASCOD2," 6th Conf. on Atmospheric Radiation, Williamsburg, VA 1986 (Abstract).
"How to Interpret the RVR Data," 2011; http://rvr.fly.faa.gov/rvr/help.html.
Husar; "The Emergence of the Bimodal . . . ," 2009; http://capita.wustl.edu/capita/CapitaReports/HistoryOfAerosolPortland/BimodalHistoryHusar2.doc.
"Manual of Runway Visual Range Observing and Reporting Practices," ICAO, 2000; Doc 9328-AN/908.

(Continued)

*Primary Examiner* — Phuong Huynh
(74) *Attorney, Agent, or Firm* — Hart IP Law & Strategies

(57) ABSTRACT

Determining optical visibility in an environment that may contain airborne dust particles is described. In one aspect, a method determines an ambient relative humidity in the environment. A near infrared wave is transmitted through a portion of the environment. An optical visibility in the environment is calculated based on the ambient relative humidity and attenuation of the near infrared wave during transmission through the environment. Various contrast thresholds are employed in the determination of optical visibility in the environment.

22 Claims, 6 Drawing Sheets

OTHER PUBLICATIONS

Kim et al.; "Comparison of laser beam propagation at 785 nm and 1550 nm in fog and haze for optical . . . ," Proc. of SPIE, 2001; 4214:26-37.

Patterson et al.; "The Relation Between Visibility and the Size-Number Distribution of Airborne . . . ," J. of Appl. Meteorology, 1976; 15:470-478.

Patterson et al.; "Measurements of Visibility vs Mass-Concentration For Airborne Soil Particles," Atmospheric Environment, 1977; 11:193-196.

Witiw et al.; "Optical Attenuation in Fog . . . ," 2009; http://www.up.ac.za/academic/geog/meteo/EVENTS/fogdew2003/PAPERS/C26.pdf.

Yaalon et al.; "East Mediterranean Trajectories of Dust-Carrying Storms from the . . . ," Saharan Dust, 1979; E. Morales, John Wiley; pp. 187-193.

Achour, Maha; "Free-Space Optics Wavelength Selection: 10 Microns Versus Shorter Wavelengths," J. Opt. Networking, 2003; 2:127-143.

Al Naboulsi et al.; "Fog attenuation prediction for optical and infrared waves," J. of SPIE, Optical Engineering, 2004; 43(2);319-329.

Bloom et al.; "Understanding the performance of free-space optics [Invited]," J. of Opt. Networking, 2003; 2(6):178-200.

Chen, C.C.; "Attenuation of Electromagnetic Radiation by Haze, Fog, Clouds, and Rain," USAF Project RAND, R-1694-PR, 1975.

Dibble, Theodore S.; "Aerosols," 2009; http://www.esf.edu/chemistry/dibble/presentation/IX_Aerosol.ppt.

"Protecting Visibility, an EPA Report to Congress," US EPA, Office of Air, Noise, and Radiation, Office of Air Quality, Planning, and Standards, 1979.

Grabner et al.; "On the relation between atmospheric visibility and . . . ," 16th IST Mobile & Wireless Comm. Summit, 2007; Budapest, Hungary.

Lorenz, Nick; "Aerosol concentration Variability at Storm Peak Laboratory," 2010, Steamboat Springs, Colorado.

"What are Aerosols," National Science Digital Library, 2011; http://www.newmediastudio.org/DataDiscovery/Aero_Ed_Center/index.htm.

"Guide to Meteorological Instruments . . . ," WMO, 2006; http://www.wmo.int/pages/prog/www/IMPO/publications/CIMOGuide/WMO-No_8.pdf.

Clough et al.; "Atmospheric radiance and transmittance—FASCOD2," 6th Conference on Atmospheric Radiation, Williamsburg, VA, May 13-16, 1986, Abstract only.

Lord, Steven D.; "A New Software Tool for Computing Earth's Atmospheric Transmission of Near- and Far-Infrared Radiation," NASA Technical Memorandum 103957, Dec. 1992.

* cited by examiner

VISIBILITY DETERMINATION IN ENVIRONMENTS CONTAINING AIRBORNE DUST PARTICLES

BACKGROUND

Dust storms and related weather events occur regularly in certain environments, such as arid regions. Dust storms and windblown dust impair optical visibility due to the airborne dust particles (and other airborne particles) generated by the storm or wind. In addition to localized sudden storms, there exist the other known global storms, which occur yearly. Cyclogenic, Frontal and Haboob storm types significantly reduce visibility. Examples are the African Haboob, American Haboob, and Khamsin in the Middle East and Asia. Impairment of optical visibility in close proximity to the ground surface is problematic for individuals and operators of vehicles and other ground-based systems as well as aircraft traffic on airport control operators. In particular, optical visibility in a substantially horizontal direction is important to many individuals due to the "line of sight" requirements for many activities and businesses.

Certain existing systems for determining optical visibility in an environment focus on vertical measurements of the location of the dust storm, such as those performed by satellite. Although these existing systems may provide useful visibility information, they do not provide optical visibility information in a substantially horizontal direction in close proximity to the ground surface. Other existing systems focus on determining optical visibility due to precipitation in wet regions using extinction or scattering coefficients of small volumes of rain or fog rather than determining optical visibility due to suspended dust particles in close proximity to the ground surface. Although these existing systems may provide useful visibility information, they do not provide optical visibility information in a substantially horizontal direction, within airborne dust particle clouds in close proximity to the ground surface.

SUMMARY

The described systems and methods relate to determining optical visibility in an environment that may contain airborne dust particles. A specific method of determining optical visibility determines an ambient relative humidity in the environment containing or close to an airborne dust cloud. An infrared wave is transmitted through a portion of the environment. The method determines attenuation of the infrared wave during transmission through the portion of the environment. An optical visibility in the environment is calculated based on attenuation of the infrared wave during transmission through the portion of the environment and the ambient relative humidity.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In the Figures, the left-most digit of a component reference number identifies the particular Figure in which the component first appears.

DETAILED DESCRIPTION

Overview

The systems and methods described herein analyze optical visibility in an environment that may contain airborne dust particles, such as those experienced during a dust storm. These systems and methods receive information regarding various atmospheric conditions and other data from one or more sensors located within or near the environment being analyzed. An optical condition is determined based on the received data associated with the environment. Example optical conditions include "standard clear air", "clear", "blown dust", "dust storm", or "severe dust storm". The described systems and methods are capable of analyzing optical visibility across a distance of 10 kilometers or longer. In a particular implementation, the optical visibility within the environment is determined in a substantially horizontal direction at a location close to the ground surface, such as several meters above the ground surface.

A particular example of determining optical visibility in an environment containing airborne dust particles determines an ambient relative humidity in the environment and determines an attenuation of an infrared wave transmitted through a portion of the environment. An optical visibility in the environment is calculated based on the ambient relative humidity and the attenuation of the infrared wave transmitted through the portion of the environment.

An Exemplary System for Determining Optical Visibility

Figure 1:
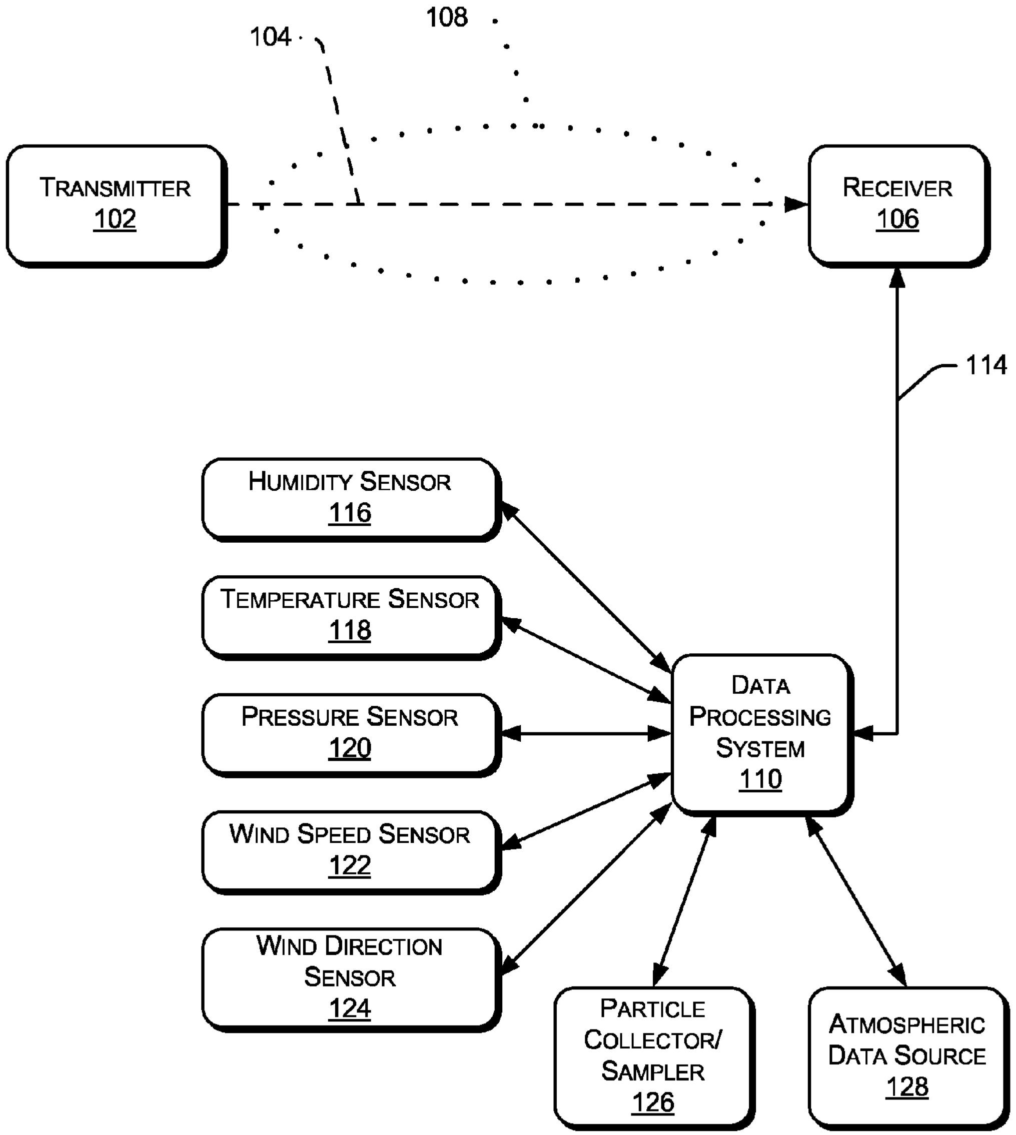
FIG. 1 shows an example arrangement of components and systems to determine optical visibility in an environment containing airborne dust particles, according to one embodiment.

FIG. 1 shows an example arrangement of components and systems to determine optical visibility in an environment containing airborne dust particles, according to one embodiment. A transmitter 102 transmits a signal 104 toward a receiver 106 through an environment 108. In a described embodiment, transmitter 102 is a single wavelength near infrared (NIR) transmitter that generates an infrared wave. Example NIR transmitters are sources that radiate electromagnetic energy at a wavelength in the range of approximately 700 to 1500 nm (nanometers). In the example of FIG. 1, signal 104 is an infrared wave having a wavelength of approximately 750 nm. Receiver 106 is a near infrared receiver capable of receiving and processing signal 104 generated by transmitter 102. In alternate embodiments, signal 104 has a wavelength in the range of 750 to 850 nm.

In the example of FIG. 1, environment 108 is an outdoor environment that may periodically experience airborne dust particles, dust storms, windblown particles, or similar weather-related events that generate a significant number of airborne dust particles and other airborne particles. These airborne dust particles can impair the optical vision of an individual in that environment. As discussed herein, the spacing between transmitter 102 and receiver 106 may range from a few meters to many kilometers.

A data processing system 110 communicates with transmitter 102 and receiver 106 via communication links 114. The data processing system 110 communicates with transmitter 102 through communication signal 104 and/or 114. Communication link 114 may be a wired communication link, wireless communication link, or a combination thereof. Data processing system 110 manages the transmission of signals from transmitter 102 and receives the corresponding signals via receiver 106. Any attenuation or other modification of signal 104 during transmission through environment 108 is detected by data processing system 110 and used in determining optical visibility in environment 108, as discussed below.

Data processing system 110 also receives atmospheric data and other information from various sensors, data sources and other devices. For example, data processing system 110 receives ambient relative humidity data from a humidity sensor 116 and receives ambient temperature data from a temperature sensor 118. Data processing system 110 also receives atmospheric pressure data from a pressure sensor 120, wind speed data from a wind speed sensor 122 and wind direction information from a wind direction sensor 124. Additional data is received by data processing system 110 from a particle collector/sampler 126 that collects and/or samples airborne particles, such as dust particles. In particular embodiments, one or more atmospheric data sources 128 are used to provide various types of atmospheric data, including any of the data provided by sensors 116-124. Atmospheric data sources 128 are, for example, remote data sources that provide a variety of atmospheric data for multiple geographic regions. The data received from the various sensors 116-124, data sources 128 and other devices 126 discussed herein is used by data processing system 110 when determining optical visibility in environment 108. Sensors 116-124, particle collector/sampler 126 and atmospheric data source 128 communicate with data processing system 110 via wired communication links, wireless communication links, or a combination thereof.

Although multiple sensors, systems and devices are shown in FIG. 1, any two or more of these sensors, systems and devices may be combined into one or more components. For example, humidity sensor 116 can be combined with temperature sensor 118 and pressure sensor 120 into a single component. In a particular implementation, sensors 116-124 are combined into a single atmospheric sensing system. Additionally, data processing system 110 may be combined with any of the sensors, systems and devices shown in FIG. 1. The various components shown in FIG. 1 can be arranged in any manner and positioned in separate geographic locations. For example, certain sensors may be located near transmitter 102 while other sensors are located near receiver 106, and data processing system 110 is located distant from both transmitter 102 and receiver 106. Regardless of device positions, the transmitter-receiver path is aligned so that the line of the infrared wave is not in the same direction of the rays of the moving sun.

Particular examples discussed herein refer to near infrared transmitters, near infrared receivers, and near infrared signals or waves. Alternate embodiments may use other types of transmitters, receivers, and/or signals to implement the systems and methods described herein.

Figure 2:
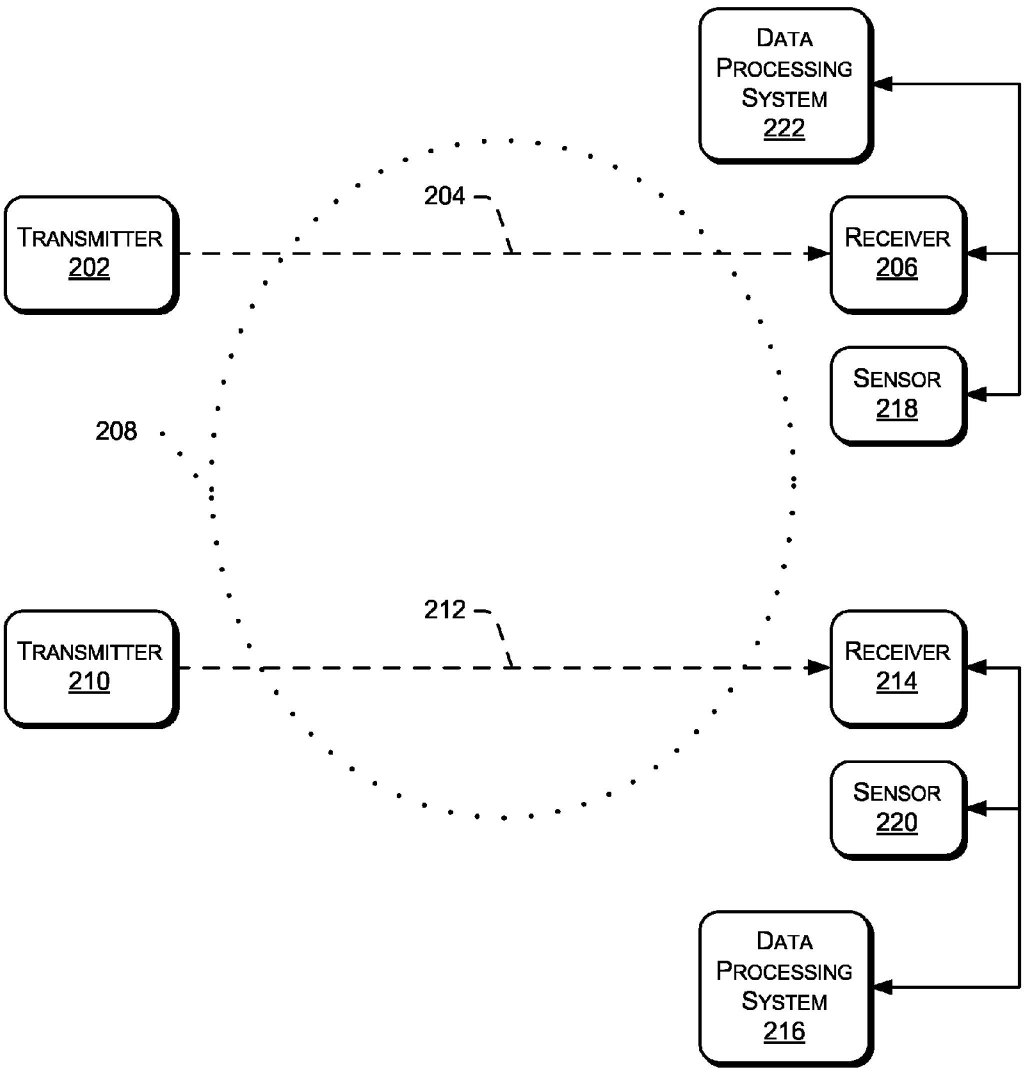
FIG. 2 shows another example arrangement of components and systems to determine optical visibility in an environment containing airborne dust particles, according to one embodiment.

FIG. 2 shows another example arrangement of components and systems to determine optical visibility in an environment containing airborne dust particles, according to one embodiment. In this example, a transmitter 202 transmits a signal 204 through an environment 208 toward a receiver 206. The path followed by signal 204 may be referred to as the "transmission path" of the signal. As discussed above with respect to FIG. 1, transmitter 202 is a near infrared transmitter capable of generating infrared waves having wavelengths of approximately 750 nm. Receiver 206 is a near infrared receiver capable of receiving and processing signal 204 generated by transmitter 202.

Additionally, a transmitter 210 transmits a signal 212 through environment 208 toward a receiver 214. As discussed above, transmitter 210 is a near infrared transmitter capable of generating infrared waves having wavelengths of approximately 750 nm. Receiver 214 is a near infrared receiver capable of receiving and processing signal 212 generated by transmitter 210.

Environment 208 is an outdoor environment that may experience airborne dust particles, dust storms, windblown particles, or similar weather-related events that generate a significant number of airborne dust particles and other airborne particles. As discussed above with respect to FIG. 1, these airborne dust particles can affect the optical vision of an individual in that environment. The spacing between transmitter 202 and receiver 206 may range from a few meters to many kilometers. Similarly, the spacing between transmitter 210 and receiver 214 may range from a few meters to many kilometers. In a particular embodiment, receiver 206 is positioned a distance from transmitter 202 (e.g., 1 km, 5 km and 10 km), and receiver 214 is positioned a different distance from transmitter 210. This embodiment allows for the determination of optical visibility in different portions of environment 208. In another embodiment, receivers 206 and 214 are positioned at varying angles with respect to transmitter 202 and 210, respectively. The embodiment of FIG. 2 also supports determination of optical visibility in different regions of environment 208.

A data processing system 216 communicates with transmitter 210, as well as receiver 214 via a communication link. Data processing system 216 manages the transmission of signals generated by transmitter 210 and receives the corresponding signals from receiver 214. Any attenuation or other modification of signal 212 during transmission through environment 208 is detected by data processing system 216 and used in determining optical visibility in environment 208, as discussed herein. Data processing system 216 also receives atmospheric data and other information from sensor 220, data sources and other devices. Sensor 220 may sense any type of atmospheric condition, such as humidity, temperature, pressure, wind speed, or wind direction, as discussed above with respect to FIG. 1. Sensor 220 can be positioned at any location within environment 208. Any number of sensors, data sources and other devices can communicate weather and atmospheric-related information to data processing system 216.

A second data processing system 222 communicates with transmitter 202 and receiver 206 via a communication link. Data processing system 222 manages the transmission of signals generated by transmitter 202 and receives the corresponding signals from receiver 206. Any attenuation or other modification of signal 204 during transmission through environment 208 is detected by data processing system 222 and used in determining optical visibility in environment 208, as discussed herein. Data processing system 222 also receives atmospheric data and other information from sensor 218, data sources and other devices. Sensor 218 may sense any type of atmospheric condition, such as humidity, temperature, pressure, wind speed, or wind direction, as discussed above with respect to FIG. 1. Sensor 218 can be positioned at any location within environment 208. Any number of sensors, data sources and other devices can communicate weather and atmospheric-related information to data processing system 222. The two systems shown in FIG. 2—each of which includes the data processing system, transmitter, receiver, and sensors—can be spaced apart from one another within the area of environment 208 to perform multiple visibility measurements at multiple locations within or proximate environment 208.

Figure 3:
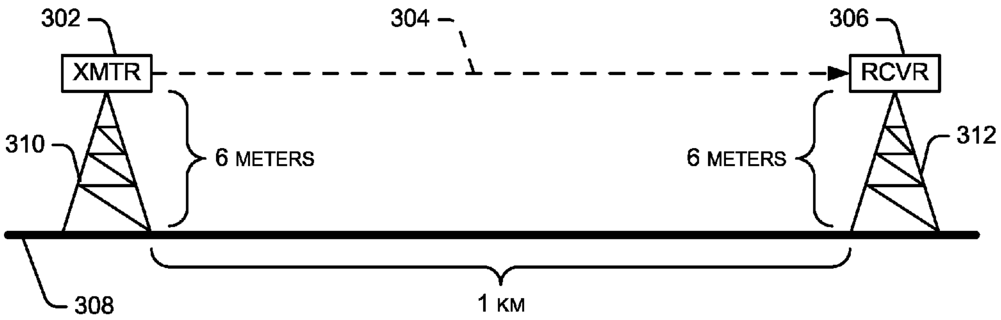
FIG. 3 shows an example transmitter and receiver spaced apart from one another, according to one embodiment.

FIG. 3 shows an example transmitter and receiver spaced apart from one another, according to one embodiment. In this example, a transmitter 302 transmits a signal 304 toward a receiver 306. As discussed herein, transmitter 302 is a near infrared transmitter, signal 304 is an infrared wave having a wavelength of approximately 750 nm, and receiver 306 is a near infrared receiver having the same wavelength and capable of receiving and processing signal 304. In the embodiment of FIG. 3, transmitter 302 is positioned approximately six meters above a ground surface 308 on a support structure 310. Similarly, receiver 306 is positioned approximately six meters above ground surface 308 on a support structure 312. A height of approximately six meters is selected to reduce the amount of vegetation and moving objects that may interfere with the transmission signal. Support structures 310 and 312 may be communication towers, existing buildings, or any other structure capable of supporting transmitter 302 and receiver 306. Support structures 310 and 312 may be dedicated for use with transmitter 302 and receiver 306, or may be used to support other devices, in addition to transmitter 302 and receiver 306.

In a particular embodiment, transmitter 302 and receiver 306 are fixed mechanically on a rigid support or a load-bearing wall to minimize mechanical vibrations or shocks. A possible structure can be implemented by having both transmitter 302 and receiver 306 firmly held by double support stainless steel construction consisting of inner monopole tubes of the order of 0.6 cm thickness and 12 cm diameter, and outer monopole tubes of 0.6 cm thickness and 25 cm diameter. The space in between the tubes is filled in with a thermal insulation, such as Mineral wool, mineral fibers, or Polystyrene to minimize the thermal effect of high ambient temperature. The monopole construction is guyed in vertical position by three adjustable stainless steel wires of 0.6 cm thickness. The structure is grounded using 10 cm×25 cm×0.3 cm solid copper bar and protected with lightening rods on top of transmitter 302 and receiver 306. Additionally, transmitter 302 and receiver 306 are protected from direct sun, direct light and high ambient temperature using a sunshade and a narrow long hood for protection against atmospheric pollution.

Various types of modifications may be applied to transmitter 302 and/or receiver 306 to minimize interference by environmental factors, such as sunlight, heat, noise, heat radiated from the ground surface, artificial lights, and so forth. As discussed above, various shades, hoods and shields can minimize certain environmental factors. Additionally, transmitter 302 and/or receiver 306 can be positioned to minimize the influence of these environmental factors on the measurement of the infrared wave and other factors.

By positioning transmitter 302 and receiver 306 approximately six meters above ground surface 308, the system determines optical visibility close to the ground surface. Optical visibility in close proximity to the ground surface is particularly useful for individuals, vehicles and other ground-based systems. In specific implementations, transmitter 302 and receiver 306 are part of an existing weather station or weather monitoring system.

As shown in FIG. 3, transmitter 302 and receiver 306 are positioned approximately one kilometer from each other. In alternate embodiments, transmitter 302 and receiver 306 can be positioned any distance from one another, as limited by physical obstacles that interfere with the transmitted signal, the curvature of the earth's surface, and so forth. Specific implementations position transmitter 302 and receiver 306 at distances of five kilometers or ten kilometers from one another. The distance between transmitter 302 and receiver 306 may be limited by the homogeneity of airborne particles and the emitting power associated with transmitter 302. The homogeneity of dust particles indicates that their characteristics are similar within the dust cloud. In most cases, homogeneity is justified since strong winds transport large quantities of dust particles long distances from their source. However, dust storms of relatively very large area (e.g., on the order of 100 km may exhibit non-homogeneity). Therefore, visibility stations are established at repeated locations to justify the homogeneity assumption, otherwise the visibility measure is location specific.

The distance between transmitter 302 and receiver 306 may be referred to as the "transmission distance" of signal 304. FIG. 3 shows one embodiment of transmitter 302 and receiver 306 placement with respect to one another and with respect to ground surface 308. FIG. 3 is not drawn to scale.

Figure 4:
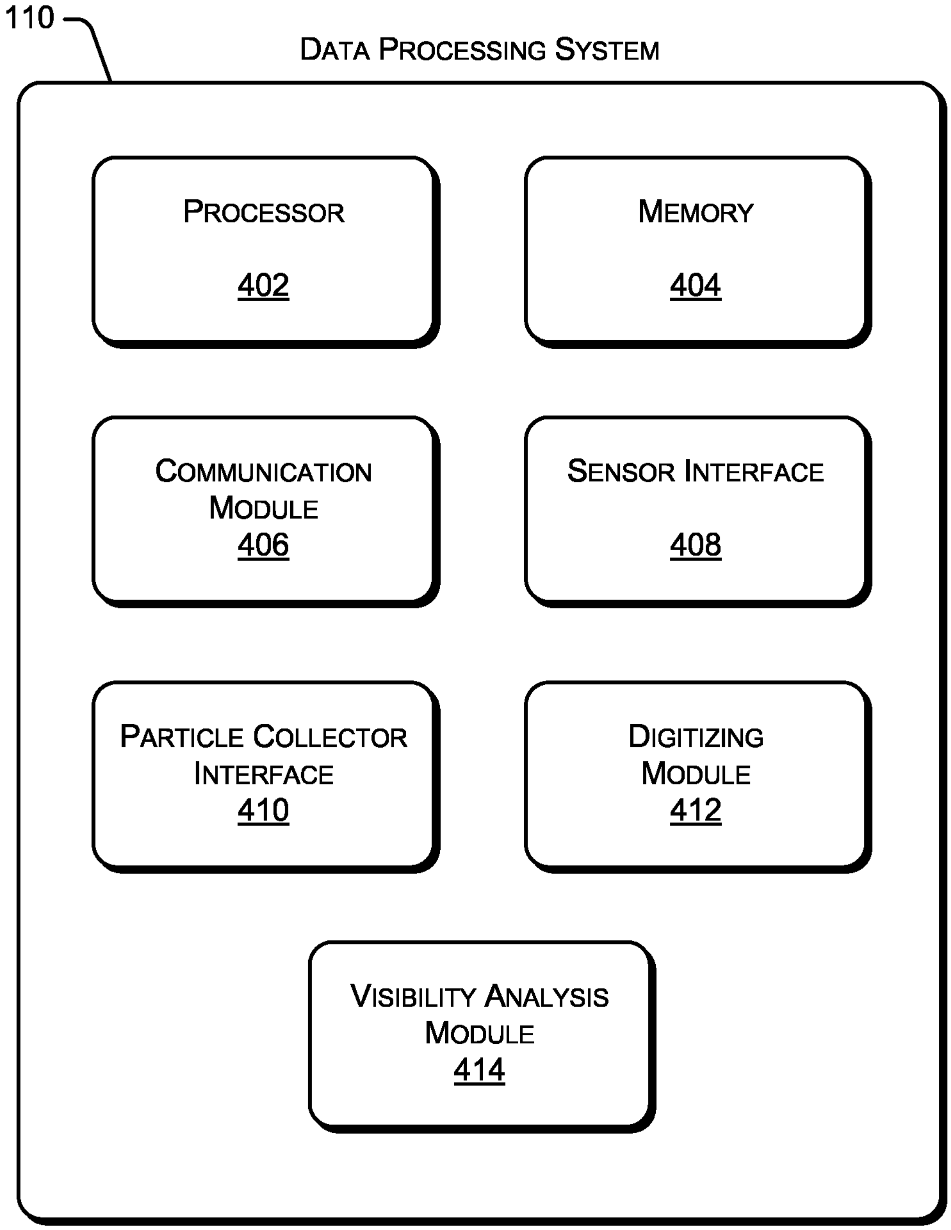
FIG. 4 is a block diagram showing various components of an example data processing system, according to one embodiment.

FIG. 4 is a block diagram showing various components of data processing system 110, according to one embodiment. Data processing system 110 includes a processor 402, a memory 404, and a communication module 406. Communication module 406 allows data processing system 110 to communicate with other devices and systems, such as transmitter 102, receiver 106 and atmospheric data source 128, shown in FIG. 1. Processor 402 executes various instructions to implement the functionality provided by data processing system 110. Memory 404 stores these instructions as well as other data used by processor 402 and other modules contained in data processing system 110.

Data processing system 110 also includes a sensor interface 408, which communicates with one or more sensors, such as sensors 116-124 discussed above with respect to FIG. 1. Sensor interface 408 communicates the data received from the sensors to one or more modules within data processing system 110, such as processor 402. A particle collector interface 410 communicates with one or more particle collectors/samplers, such as particle collector/sampler 126 shown in FIG. 1. A digitizing module 412 digitizes various signals, such as analog signals received from the receiver and from one or more sensors. The digitized signals are stored in memory 404 for future use by processor 402 or other components in data processing system 110. Digitizing module 412 may be an analog-to-digital converter or similar device. A visibility analysis module 414 applies signals received by the near infrared receiver, various sensor data, atmospheric data and other information to one or more visibility formulas to determine an optical visibility in the environment being analyzed. Additional details regarding the procedure for determining optical visibility are provided herein.

An Exemplary Procedure for Determining Optical Visibility

Figure 5:
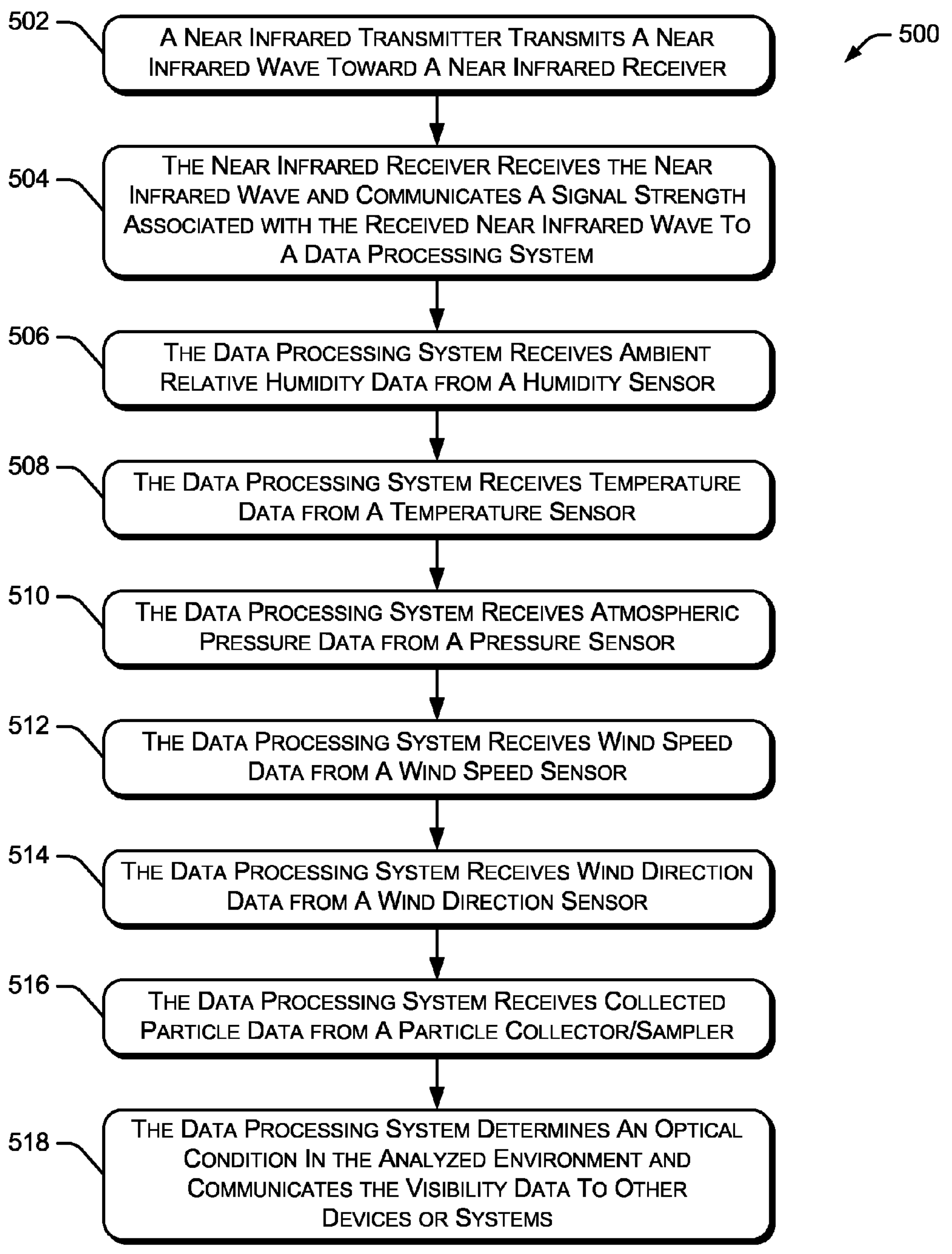
FIG. 5 is a flow diagram illustrating an example procedure for determining optical visibility, according to one embodiment.

FIG. 5 is a flow diagram illustrating an example procedure 500 for determining optical visibility, according to one embodiment. Initially, a near infrared transmitter transmits a near infrared wave toward a near infrared receiver (block 502). The emitted power of the near infrared transmitter is typically greater than 20 dBm (decibels of power referenced to one milliwatt). The near infrared receiver receives the near infrared wave and communicates a signal strength associated with the received near infrared wave to a data processing system (block 504). This signal strength is used by the data processing system to determine attenuation of the signal during transmission through the environment. Attenuation of the signal strength is used, along with other factors, to determine optical visibility in the environment. In a particular embodiment, the signal strength is determined from an automatic gain control (AGC) voltage generated by the near infrared receiver. The AGC voltage is proportional to the received intensity of the near infrared wave.

The procedure continues as the data processing system receives ambient relative humidity data from a humidity sensor (block 506) and receives temperature data from a temperature sensor (block 508). The data processing system also receives atmospheric pressure data from a pressure sensor (block 510). Next, the data processing system receives wind speed data from a wind speed sensor (block 512) and wind direction data from a wind direction sensor (block 514). The data processing system further receives collected particle data from a particle collector/sampler (block 516). Finally, the data processing system determines an optical condition in the analyzed environment and communicates the visibility data to other devices or systems (block 518). As discussed below, based on the visibility and time measurement data, the data processing system is able to calculate a probability distribution function of visibility in airborne dust. The probability distribution function is associated with the visibility variation in the environment being analyzed.

Figure 6:
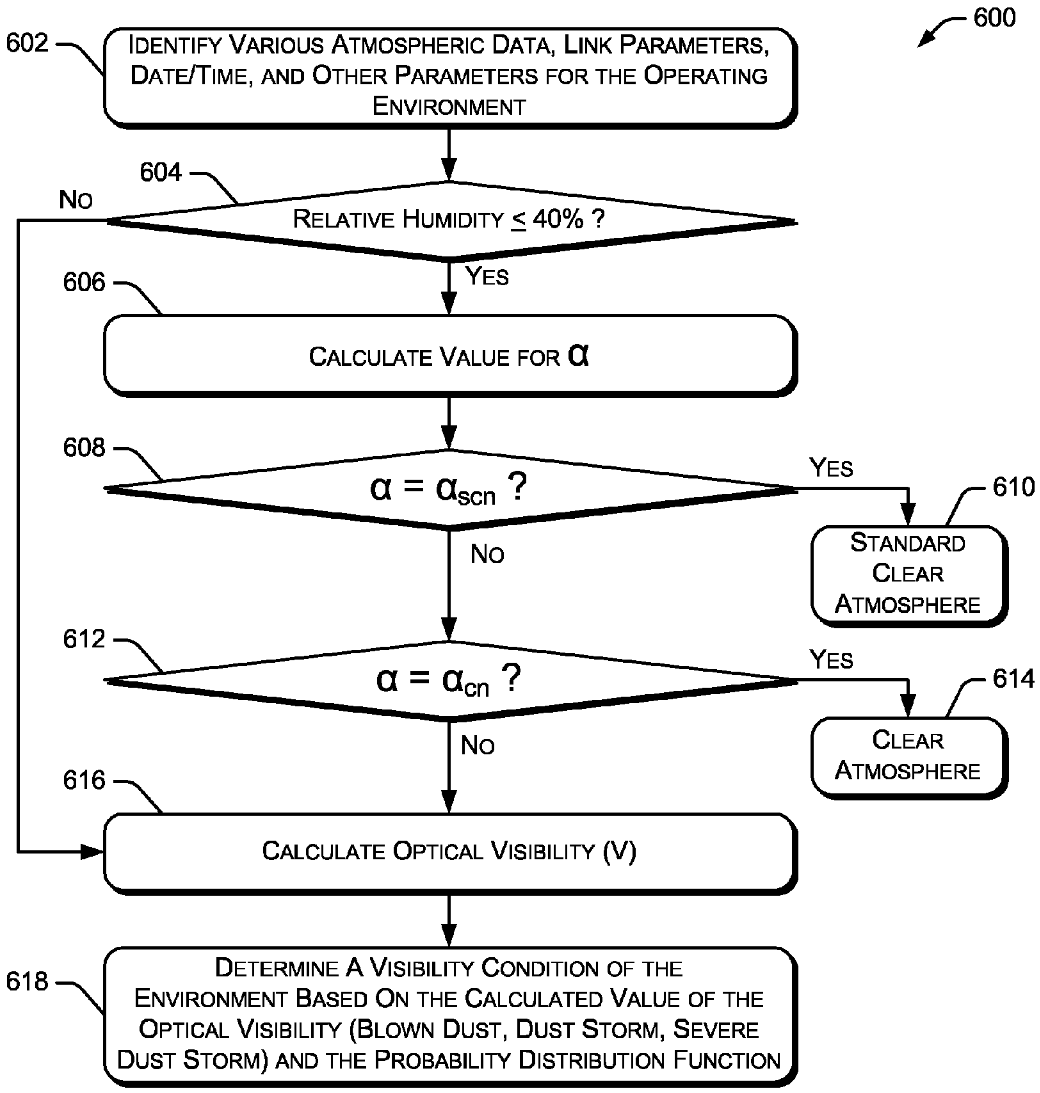
FIG. 6 is a flow diagram illustrating an example procedure for analyzing optical visibility based on various data, according to one embodiment.

FIG. 6 is a flow diagram illustrating an example procedure 600 for analyzing optical visibility based on various data, according to one embodiment. Based on the analysis described herein, procedure 600 determines an optical condition of an operating environment. The operating environment is a region having a size ranging from a few square meters to several hundred square kilometers. In a particular embodiment, the optical condition is categorized as "standard clear air", "clear", "blown dust", "dust storm", or "severe dust storm". These five categories are defined as follows:

Standard clear air: Visual range (V)<23 km

Clear air: Visual range (V)<20 km

Blown dust: Visual range (V)<11 km

Dust storm: Visual range (V)<1.0 km

Severe dust storm: Visual range (V)<0.5 km

The visual range (V) for various optical conditions depends on various factors, including the attenuation of light intensity as a result of airborne particles, such as dust particles. The visual range also depends on other factors, such as a contrast threshold (C) associated with the human eye-brain system and the nature of the object being observed by an individual. "Visual range" may also be referred to as "visibility".

Initially, procedure 600 identifies various atmospheric data, link parameters, date/time and other parameters associated with the operating environment (block 602). The procedure determines whether the relative humidity within the operating environment is less than or equal to 40% (block 604). Dust storms and similar weather-related events generally occur in dry climates (e.g., relative humidity less than 40%). Thus, the procedure of FIG. 6 is directed toward operating environments in dry climates. If the relative humidity exceeds 40%, the procedure branches to block 616 to calculate an optical visibility value at relatively higher relative humidity. If the relative humidity does not exceed 40%, the procedure continues by calculating a value for the attenuation coefficient α at wavelength 750 nm for a dry condition (block 606) using the following formula:

$$a(\lambda = 750\text{ nm})\text{dry} = \left|20\log\frac{So}{Sd}\right| \Big/ L \text{ dB/km}$$

For example, when λ=550 nm at which human eye-brain system has the highest sensitivity, the above formula is as follows:

$$\alpha(\lambda = 550\text{ nm})\text{dry} = [\alpha(\lambda = 750\text{ nm})\text{dry}]\left[\frac{750}{550}\right]^{-1.529} \text{ dB/km}$$

and $$V_{dry}(\lambda = 550\text{ nm}) = [4.3428/(\alpha(\lambda = 750\text{ nm})\text{dry} * L)][750/550]^{-1.529} \text{ km}$$

In this example, the optical visibility in a dry environment for the wavelength λ=550 nm (where the human eye-brain system has the highest sensitivity) is calculated as:

$$V_{dry}(\lambda = 550\text{ nm}) = \left[\frac{2.7028}{a(\lambda = 750\text{ nm})\text{dry} * L}\right]\left[\ln\left(\frac{1}{C}\right)\right] \text{ km}$$

In the above formulas, α represents an attenuation coefficient (dB/km) associated with the near infrared wave communicated from the near infrared transmitter to the near infrared receiver. L is the distance between the near infrared transmitter and the near infrared receiver, V is the resulting visibility measured in kilometers. $S_o$ represents the AGC output voltage from the infrared receiver during normal (standard clear air) conditions. The value of $S_o$ is proportional to the received infrared wave intensity $I_o$ in standard clear air conditions. $S_d$ represents the AGC output voltage from the near infrared receiver during "blown dust" conditions. The value of $S_d$ is proportional to the received near infrared wave intensity $I_d$ in "blown dust" conditions.

As used in the discussion of FIG. 6, $\alpha_{scn}$ is the value of α for a "standard clear air" condition and $\alpha_{cn}$ is the value of α for a "clear" condition. If the value of α equals $\alpha_{scn}$ (block 608), the procedure branches to block 610, which sets the current optical condition of the environment as "standard clear air". If the value of α equals $\alpha_{cn}$ (block 612), the procedure branches to block 614, which sets the current optical condition of the environment as "clear".

If the value of α is not greater than $\alpha_{cn}$, procedure 600 calculates the optical visibility value at relative humidity RH % (block 616), represented by V, according to the following formula:

$$V_{RH\,\%(\lambda=550\,nm)} = [V_{dry(\lambda=550\,nm)}][0.3948][\exp-(0.0211*\text{RH }\%)]\text{km}$$

The visual range (V) for various optical conditions depends on various factors, such as the attenuation of light intensity as a result of airborne particles, such as dust particles. The visual range also depends on a contrast threshold (C) associated with the visual perception characteristics of the human eye-brain system and the nature of the object being observed by an individual. The visual range is calculated using the above formula for a variety of contrast thresholds (C), such as 0.02, 0.031 and 0.055. The values of C vary between different individuals, but are based on the three preset values of C=0.02, C=0.031 and C=0.055. The three values of C are employed to cover the variations due to disparity of human thresholds, non-ideal black targets, and non-homogeneous atmospheric aerosol. The system will give three different values of visibility corresponding to the three different values of C that are relevant to three types of applications. A specific application will determine the selected visibility result. In the example of FIG. 6, “n” represents a contrast ratio flag. When n=2 then C=0.02, when n=3 then C=0.031, and when n=5 then C=0.055.

RH % in the above formula represents the relative humidity read by a humidity sensor or similar device in or near the operating environment. Relative humidity (RH %) causes the dust particles to be wet. The wet dust particles cause more attenuation of the transmitted signal (due to their size and refractive index increase) than dry dust particles.

After calculating the visual range (V), procedure 600 determines an optical condition of the environment based on the visual range and the probability distribution function (block 618). The optical condition includes “blown dust”, “dust storm”, or “severe dust storm”. Using the obtained visibility variations and time, the probability distribution function of the visibility can be obtained. The various data collected and/or calculated during the operation of procedure 600 is also stored for future access and analysis.

CONCLUSION

Although the systems and methods for determining optical visibility have been described in language specific to structural features and/or methodological operations or actions, it is understood that the implementations defined in the appended claims are not necessarily limited to the specific features or actions described. Rather, the specific features and operations of determining optical visibility are disclosed as exemplary forms of implementing the claimed subject matter.

The invention claimed is:

1. A method for determining optical visibility in an environment that contains airborne dust particles and sand particles of an arid climate, the method comprising:

determining an ambient relative humidity in the environment;

transmitting an infrared wave through a portion of the environment;

determining an attenuation of the infrared wave during transmission through the portion of the environment;

determining a length of a transmission distance associated with a transmission path of the infrared wave; and calculating an optical visibility in the environment in an environment containing airborne dust particles and sand particles of an arid climate based on the ambient relative humidity, attenuation of the infrared wave during transmission through the portion of the environment, and the length of the transmission distance associated with the transmission path of the infrared wave.

2. A method as recited in claim 1 wherein the infrared wave is transmitted in a substantially horizontal direction through the portion of the environment.

3. A method as recited in claim 1 wherein the infrared wave is transmitted through the portion of the environment in proximity to a ground surface within the environment.

4. A method as recited in claim 1 wherein the infrared wave is transmitted a distance of approximately one kilometer.

5. A method as recited in claim 1 wherein the infrared wave is transmitted a distance in the range of one kilometer to ten kilometers.

6. A method as recited in claim 1 wherein the infrared wave has a wavelength of approximately 750 nanometers.

7. A method as recited in claim 1 further comprising applying a plurality of human vision contrast thresholds when calculating the optical visibility in the environment.

8. A method as recited in claim 1 wherein determining an attenuation of the infrared wave includes an automatic gain control in an infrared receiver assessing the attenuation of the infrared wave.

9. A method as recited in claim 1 further comprising positioning a receiver of the infrared wave to minimize ambient interferences from other environmental factors.

10. A method as recited in claim 1 further comprising determining other atmospheric conditions present in the environment that affect optical visibility.

11. A method as recited in claim 1 further comprising determining a probability distribution function associated with visibility variation in the environment.

12. A method for determining optical visibility in an environment containing airborne dust particles and sand particles of an arid climate, the method comprising:

determining an ambient relative humidity in the environment containing airborne dust particles and sand particles of an arid climate;

transmitting a near infrared wave from an infrared transmitter to a near infrared receiver, wherein the near infrared wave is transmitted through a portion of the environment containing airborne dust particles and sand particles of the arid climate in a substantially horizontal direction;

determining an attenuation of the near infrared wave resulting from transmission through the portion of the environment;

determining a length of a transmission distance between the near infrared transmitter and the near infrared receiver; and calculating an optical visibility in the environment containing airborne dust particles and sand particles of the arid climate based on the ambient relative humidity, the attenuation of the near infrared wave resulting from transmission through the portion of the environment containing airborne dust particles and sand particles of the arid climate, and the transmission distance between the near infrared transmitter and the near infrared receiver.

13. A method as recited in claim 12 wherein the near infrared wave is transmitted proximate to a ground surface within the environment containing airborne dust particles and sand particles of the arid climate.

14. A method as recited in claim 12 wherein the near infrared wave is transmitted approximately six meters above a ground surface within the environment containing airborne dust particles and sand particles of the arid climate.

15. A method as recited in claim 12 wherein the length of the transmission distance between the near infrared transmitter and the near infrared receiver for the infrared wave is a distance in the range of one kilometer to ten kilometers.

16. A method as recited in claim 12 wherein the near infrared wave has a wavelength of approximately 750 nanometers.

17. A method as recited in claim 12 further comprising determining a specific human vision contrast threshold associated with the environment containing airborne dust particles and sand particles of the arid climate from a plurality of human vision contrast thresholds.

18. A method as recited in claim 17 further comprising applying the specific human vision contrast threshold when calculating the optical visibility in the environment.

19. A data processing system for determining optical visibility in an environment containing airborne particles, the data processing system comprising:

a memory;

a sensor interface to receive atmospheric data associated with the environment, wherein the atmospheric data includes ambient relative humidity; and a processor coupled to the memory and the sensor interface, the processor to calculate an optical visibility in the environment based on the atmospheric data associated with the environment, an attenuation of a near infrared wave during transmission through a portion of the environment, and a length of a transmission distance associated with a transmission path of the near infrared wave using a single transmitter/receiver pair.

20. A data processing system as recited in claim 19 further comprising a digitizing module to digitize signals received from the sensor interface.

21. A data processing system as recited in claim 19 wherein the processor calculates the attenuation of the near infrared wave during transmission through a portion of the environment based on data received from a near infrared receiver.

22. A data processing system as recited in claim 19 further comprising a communication module to receive atmospheric data from a remote data source.

* * * * *